United States Patent [19]
Bartorelli et al.

[11] Patent Number: 5,824,640
[45] Date of Patent: Oct. 20, 1998

[54] SUBSTANCES OF POLYPEPTIDE NATURE USEFUL IN HUMAN THERAPY

[75] Inventors: Alberto Bartorelli; Angela Turiano, both of Milan, Italy

[73] Assignee: Zetesis S.p.A., Milan, Italy

[21] Appl. No.: 403,121

[22] Filed: Mar. 13, 1995

Related U.S. Application Data

[63] Continuation of Ser. No. 74,806, filed as PCT/EP91/02354, Dec. 9, 1991 published as WO92/10197, Jun. 25, 1992, abandoned.

[30] Foreign Application Priority Data

Dec. 11, 1990 [IT] Italy ................................. 22341A/90

[51] Int. Cl.[6] ........................... A61K 38/02; C07K 14/46
[52] U.S. Cl. ............................ 514/12; 530/350; 530/353
[58] Field of Search ................................... 530/350, 353; 514/12

[56] References Cited

U.S. PATENT DOCUMENTS 4,383,985  5/1983  Bartonelli .
5,182,257  1/1993  Zeppezauer et al. ................... 514/2

FOREIGN PATENT DOCUMENTS 0210588  2/1987  European Pat. Off. .

OTHER PUBLICATIONS

Watson et al., "Molecular Biol. of the gene", Benjamin/Cummings Pub Co Inc., 1987, pp. 677–679.
Goding, "Monoclonal Antibodies: Principles and Practices", Academic Press, 1986, pp. 59–103, 281–293.
Steiner et al., Biotechnology, 11: 644, 1993 Whitley, Inf. Agents and Dis., 1: 119–120, 1992.
Bartorelli et al., J. Tum. Mark. Onc., 9:37–47, 1994 (Abstract thereof).
Harris et al., TIBTECH, 11:42–44, 1993 Waldman, Science, 252:1657–1662, 1991.
Chemical Abstracts, vol. 106, No. 23, issued Jun. 8, 1987, Abstract #194 775g, T. Nishihara, et al—"Novel Antitumor Polypeptide Production" etc.
Chemical Abstracts, vol. 102, No. 3, issued Jan. 21, 1985, Abstract No. 17 760v, T. Ikeda, et al—"General Methods for Isolation of Acetic Acid—" etc.
Schweizerische Rundschau Fur Medizin Praxis, vol. 79, No. 16, Apr. 17, 1990, A. Kast et al, "Faktor AF2—die vierte Saule in der Tumortherapie" etc., pp. 498–502.

*Primary Examiner*—Thomas M. Cunningham
*Assistant Examiner*—Martha Lubet
*Attorney, Agent, or Firm*—Griffin, Butler, Whisenhunt & Szipl

[57] ABSTRACT

Substances of polypeptide nature are obtainable by extraction with $HClO_4$ and 3M KCl from animal tissue homogenates. The substances have the characteristics of (a) molecular weights ranging from 10,000 to 50,000 daltons (by polyacrylamide gel electrophoresis); (b) are capable of inducing the formation of antibodies which specifically bind in vivo or in vitro antigens which are present in human tumoral cells, when administered to different animal species; (c) are capable of decreasing or inhibiting pain; (d) induce an effect of cell lysis; and (e) inhibit or slow tumor growth, when administered to humans affected by malignant tumors of different kinds.

3 Claims, 12 Drawing Sheets

SUBSTANCES OF POLYPEPTIDE NATURE USEFUL IN HUMAN THERAPY

This application is a continuation, of Ser. No. 08/074,806, filed Jul. 28, 1993, now abandoned which is a 371 of PCT/GP91/02354 filed Dec. 9, 1991, published as WO92/10197, Jun. 25, 1992.

The present invention concerns substances obtainable by extraction of animal tissues, particularly from goat or ovine tissues, which substances are useful in therapy and in diagnostics. More particularly, the invention refers to substances having surprising biological properties which make them useful in oncological therapy (or at least in supporting therapy of the neoplastic disease) and in diagnostic applications of the immunohistological and immunoserological kind.

BACKGROUND OF THE INVENTION

Besides the ongoing research for "exogenous" anti-tumor drugs of synthetic, semi-synthetic, fermentative or extraction origin, more and more attention has recently been paid to a new approach based on the study of physiological compounds, naturally occurring in the body, which are able to inhibit the growth of tumoral cells through direct cytotoxic effects or by means of complex interactions with the humoral or cellular components of the immune system.

Within this trend, remarkable research efforts are paid, for instance, to interferons, tumor necrosis factor (TNF), cytokines and lymphokines such as interleukins, immunotoxins deriving from conjugates of monoclonal antibodies with cytotoxic substances of different kind, etc.

Poor attention has up to now been paid to the search for compounds which can be extracted from xenogenic tissues. A factor, named AFC, obtainable by extraction of sheep and lambs embryos, has been studied since 1940 but, apparently, without applicative results worthy of further investigation (Schweiz-Rundsch-Med. Prax. 1990 79 (16): 498–502).

SUMMARY OF THE INVENTION

Starting from previous studies of the inventor on the presence of substances having unusual immunological properties (Biomed. Pharmacother. 1987, 41, 2–5) in the serum of patients affected by tumors, it has now been found that substances of polypeptide nature can be extracted from animal tissues, particularly from those of goats and sheeps, which substances have the following surprising properties:

they can induce the formation of antibodies able to recognize human tumor antigens;

they can decrease or inhibit neoplastic pain and they can induce an effect of cell lysis and inhibit or slow down the tumor growth, when administered to humans affected by malignant tumors of different kinds.

The meaning of the term "substances of polypeptide nature" as used in the present disclosure, should be intended to comprise any kind of polypeptide compound, such as proteins, glycoproteins, mucoproteins, and the like.

The substances of the present invention may be obtained by extracting, preferably in acidic conditions, homogenates of animal tissues, particularly of goats and sheeps. The use of goat organs is particularly preferred; preliminary tests do not exclude the use of other animal species, for instance sharks.

Extraction tests of liver and intestine confirmed the presence, in these organs, of the substances having the above reported characteristics; therefore it can be assumed that their distribution is ubiguitary and not limited only to one organ or organ groups. Due to practical reasons, reference is hereinafter specifically made to goat liver, which is more convenient to treat and more easily available than other organs.

The extraction of the substances of the invention comprises the following steps:

a) homogenization of tissues and organs with usual techniques;

b) treatment of the homogenates with strong inorganic acids at temperatures lower than 10° C., or extractive methods (detergents, urea, etc.);

c) centrifugation and dialysis against water;

d) treatment with hypertonic solution, centrifugation or membrane filtration and dialysis against water and than against saline buffer (PBS);

e) ultrafiltration on membranes having cut-off 10,000 D, up to a concentration of about 1 mg/ml of proteins;

f) optional further purification by gel-chromatography.

In step b) 2N perchloric acid at a temperature of about 4° C. is preferably used.

In step d) a 3M KCl solution is used and treatment is carried out for about 24 hours at 4° C. The dialysis, filtration or centrifugation operations are carried out according to usual methods.

The obtained substance may directly be used according to the invention.

It will accordingly be treated with usual methods to make it sterile and apyrogenic for the administration to patients or animals in form of suitable pharmaceutical compositions, such as those disclosed in Remington's Pharmaceutical Sciences Handbook, Mack Pub. Co., N.Y., USA.

Examples of said compositions comprise vials of lyophylized active principles which can be dissolved prior to the use with sterile saline solutions, solutions or suspensions in aqueous or oily sterile solvents and similar compositions suitable for the in vivo administration.

DESCRIPTION OF PREFERRED EMBODIMENTS

Preliminary clinical tests, hereinafter summarized, allow the assumption that the substances of the invention may be administered in a wide range of doses, for instance from 0,1 to 100 mg/day for consecutive days or at different intervals (e.g. once a week, once a month or even longer periods). Particularly, it has been noticed that using substances extracted from goat liver, hereinafter referred to as LGE, a single administration of an amount of 1–3 mg of dry substance (1–3 ml of solution) can be sufficient to obtain surprising and very fast results in patients affected by tumor pathologies.

A second administration after about 30 days may sometimes produce advantageous effects. It cannot however be ruled out that the ongoing tests could indicate changes in posology and treatment schedule, determined according to the pathology and the patient's conditions.

The following example further illustrates the invention.

EXAMPLE 100 g of male goat liver were homogenized in a blade homogenizer, the homogenate was re-suspended in distilled water to a final volume of 400 ml.

400 ml of 2N $HClO_4$ were dropped into said suspension in about 20 minutes at 4° C. and stirring for further 30 minutes. After centrifugation at 10,000 g for 20 minutes, the precipitate was discarded and the supernatant was dialyzed against tap water and then against distilled water.

After dialysis, powdered KCl was added to the obtained liquid till obtaining a 3 molar solution and the mixture was stirred for 24 hours at 4° C. After centrifugation at 100,000 g for 1 h., the supernatant was dialyzed against distilled water and phosphate buffer (PBS).

The obtained solution (800 ml) has a mean protein concentration of 200 $\mu$g/ml according to the Lowry method.

The solution was concentrated by ultrafiltration to a concentration of 1 mg/ml, it was named LGE and directly used for the clinical tests, hereinbelow summarized, making always reference to the abbreviation LGE.

Figure 1:
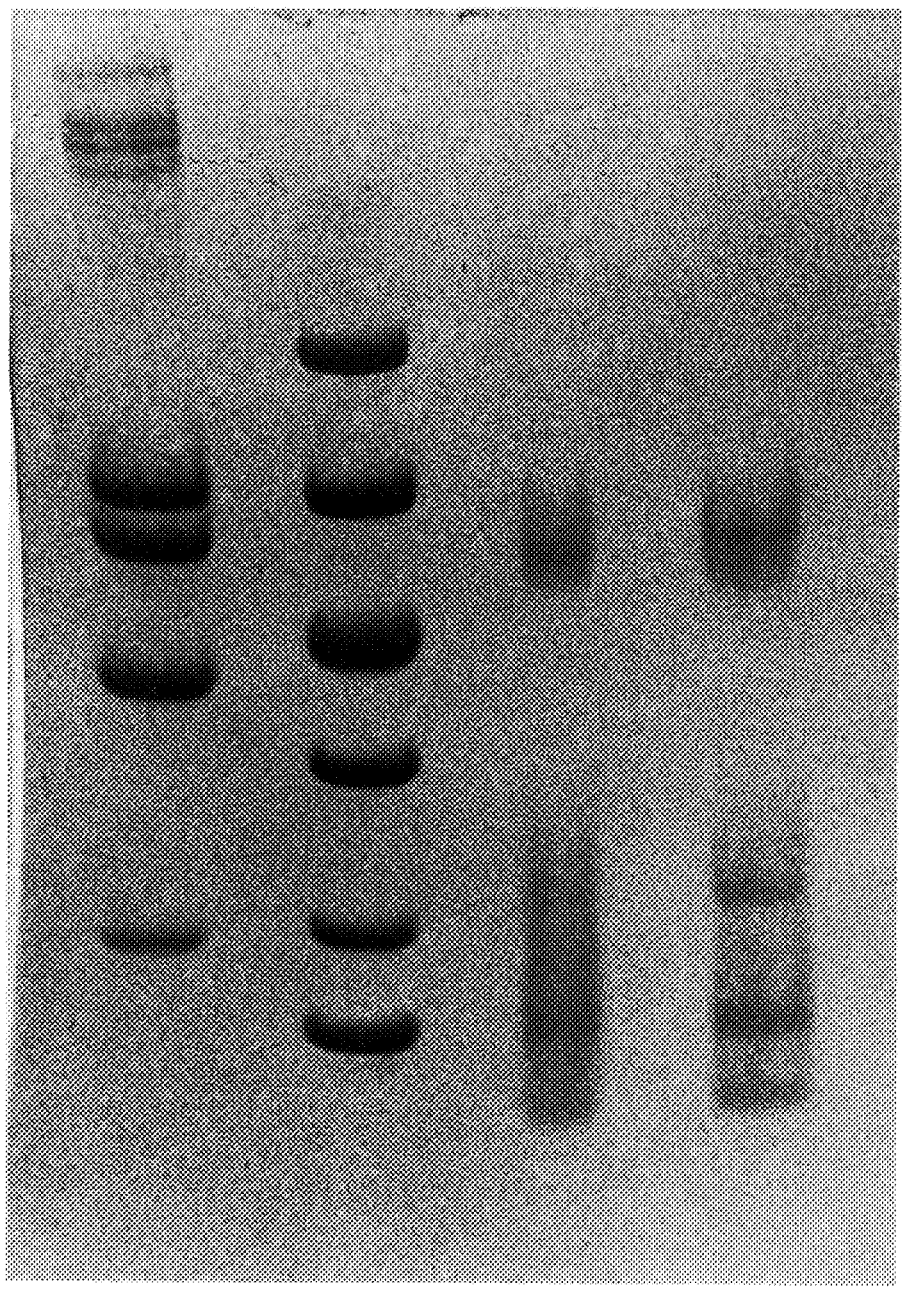
FIG. 1 is a diagram of a PAGE 4/30 test results of the Example.

This product was assayed in PAGE 4/30 where 4 main bands were evident (FIG. 1): from the calibrating curve obtained from the parameters of the standards, the molecular weights of the 4 main bands were calculated:

$1^{st}$ band:=about 50,000 d $2^{nd}$ band:=about 20,000 d $3^{rd}$ band:=about 14,800 d $4^{th}$ band:=about 12,000 d As a purification step subsequent to the LGE extraction, a ion-exchange chromatography was used, according to the following method. About 20 ml of LGE were dialyzed against a phosphate buffer ($Na_2HPO_4$—$NaH_2PO_4$ 0.01M, pH 6.5). After dialysis the sample was filtered through a 0.45 $\mu$m filter and then changed on a TSK DEAE (separation column) SPW 7.5×75 mm column, equilibrated in the same dialysis buffer, with a flow of 30 ml/hour.

The column elution was continued for 100 minutes with the same flow and buffer.

A linear gradient of phosphate buffer at pH 6.5 is started from an initial molarity of 0.01M to a final molarity of 0.1M, said gradient having a duration of 100 minutes and the operative flow being kept at 30 ml/hour.

From the eluate, 0,5 ml fractions were collected and the different zones corresponding to the various peaks were pooled.

Figure 2:
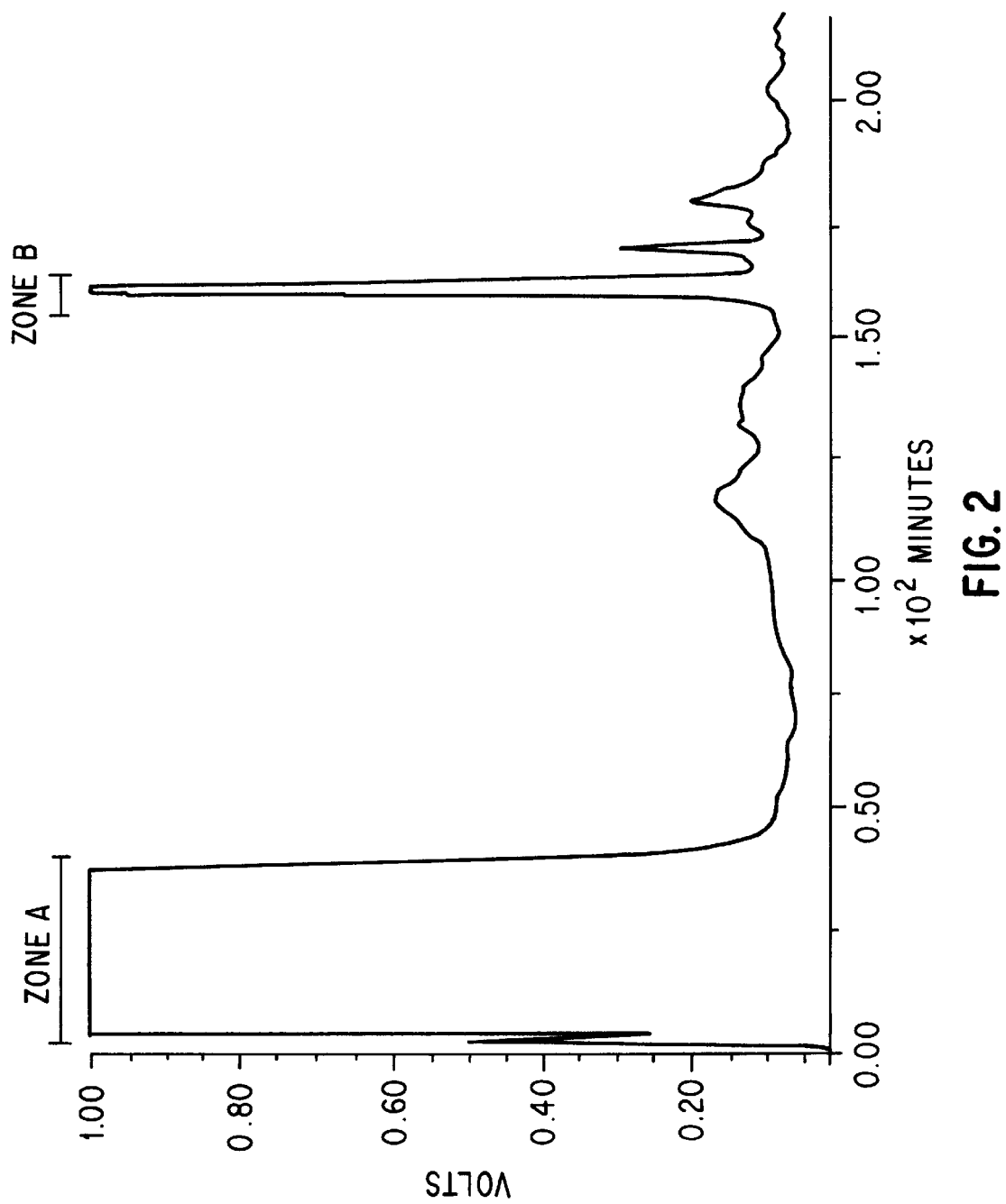
FIG. 2 is a chromatogram of the results of the Example.

As it can be derived from the chromatogram (FIG. 2) various protein fractions were obtained which were singularly assayed in PAGE PAA4/30 to evaluate the components thereof. The starting buffer, defined as zone A, and the gradient fraction having the highest protein concentration, defined as zone B, were preliminary considered as more interesting since low molecular weight proteins were mostly present in the zone A whereas the proteins having molecular weight of 50,000 daltons were present in higher concentrations in the zone B.

Figure 3:
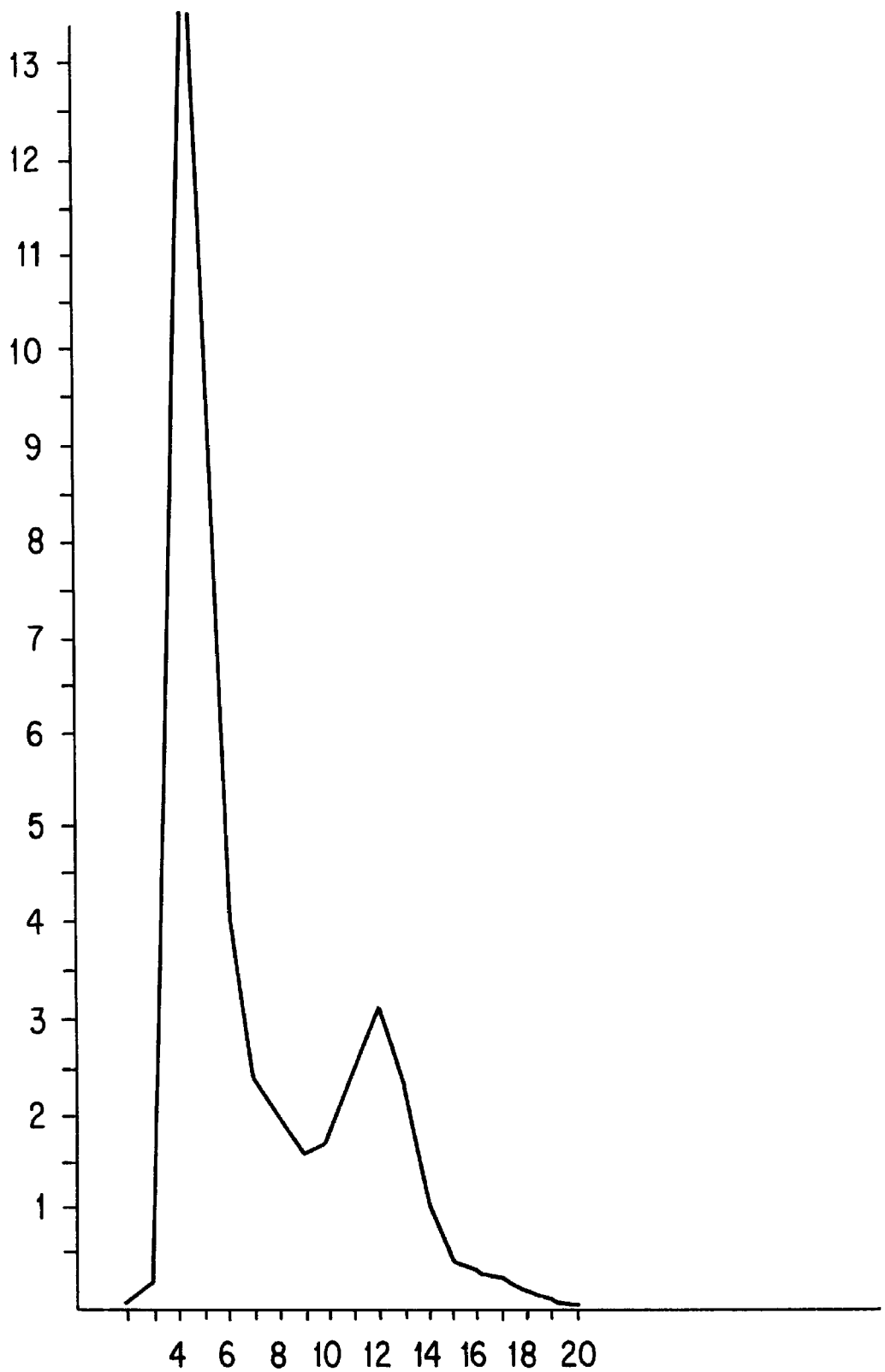
FIGS. 3 and 4 show results of samples of the Example labelled with $I^{125}$.
Figure 4:
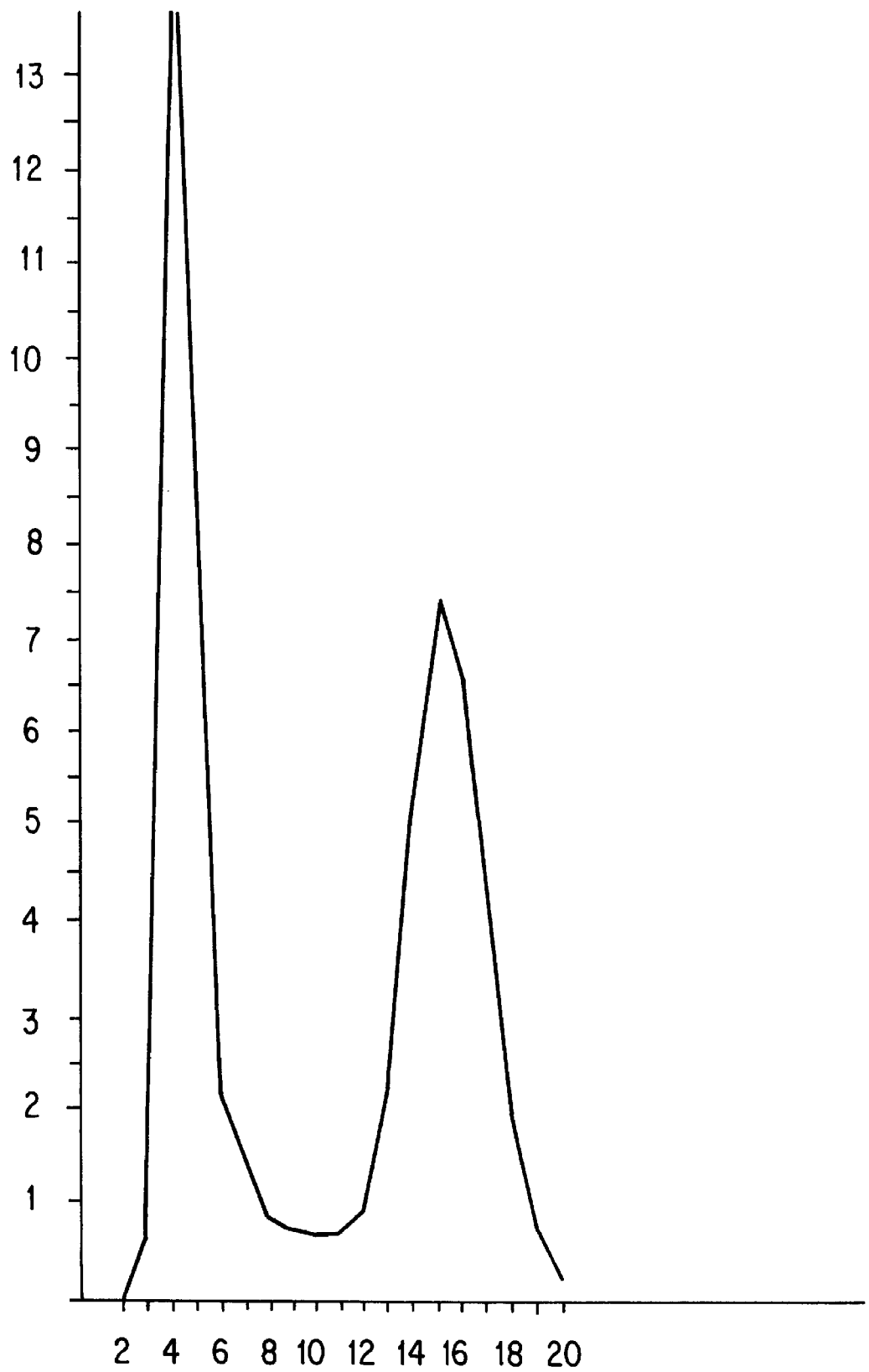

Those two samples, zones A and B, were subsequently labelled with $I^{125}$ (FIG. 3 and 4) and used in RIA. In order to make available to the clinical experimentation, in practically useful amounts, zones A and B to be separately administered, the purification of larger amounts of LGE was required.

A zone preparative gel DEAE-SEPHADEX (separation column), equilibrated and eluted under the same conditions as the DEAE SPW column, was used in FPLC.

800 mg of LGE were purified by this column and 42 mg of zone A and 15 mg of zone B were obtained.

Figure 5:
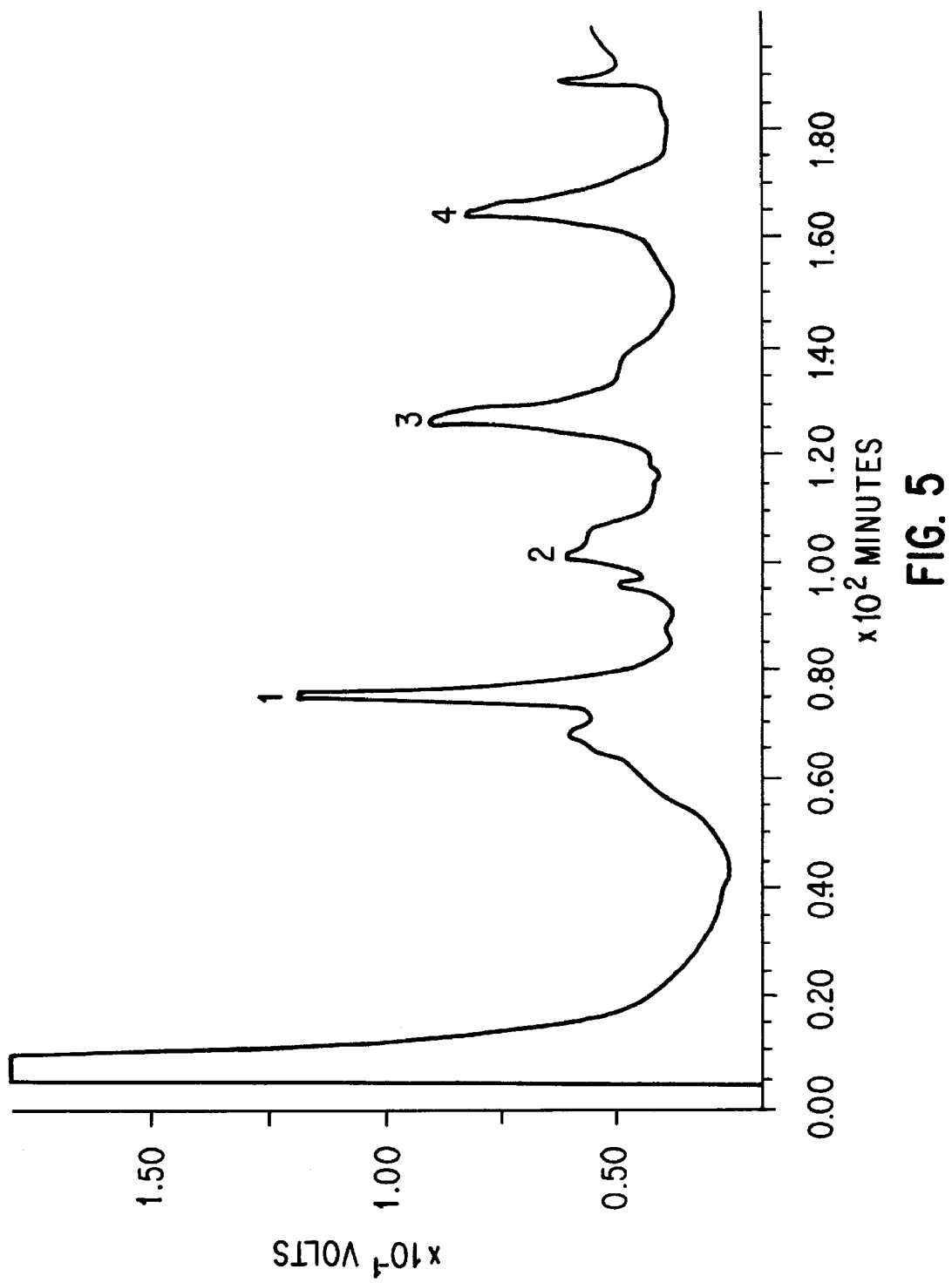
FIG. 5 is a chromatogram of test results of the Example.
Figure 6:
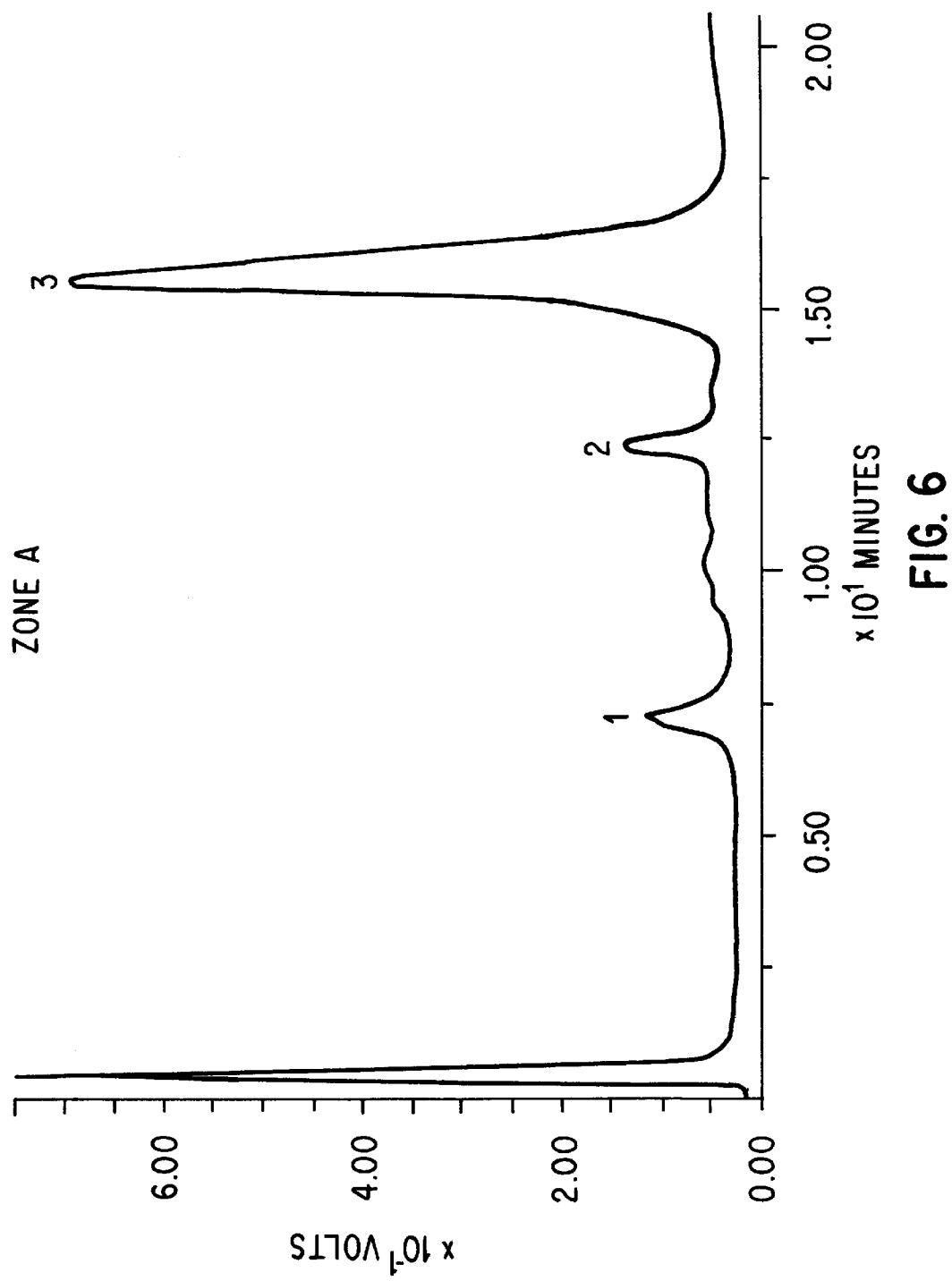
FIGS. 6 and 7 are chromatograms of test results of the Example.
Figure 7:
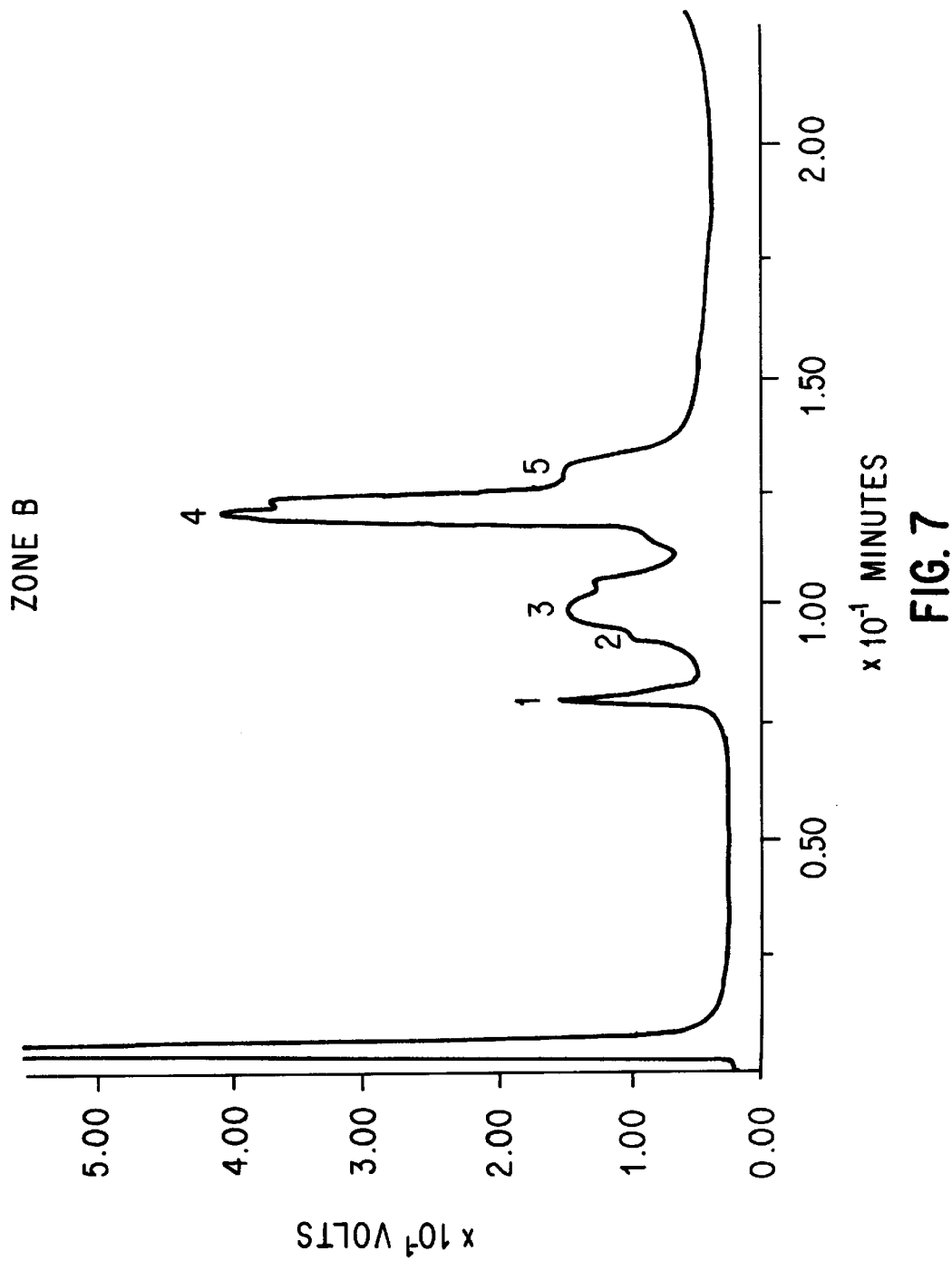

Subsequently a portion of LGE batch 2/90 was analysed in reverse phase with an AQUAPORE BUTYL (analyzer (30×4.6 mm 7U) of Applied Biosystem, using as eluents water and acetonitrile containing 0.05% TFA in linear gradient of acetonitrile from 25 to 55% in 15 minutes. The chromatogram recorded at 220 mm is shown in FIG. 5. A portion of zone A and zone B samples deriving from DEAE SEPHACELL (separation column) was chromatographed in reverse phase under the same conditions reported for crude LGE (FIGS. 6 and 7).

Examining the chromatograms of crude LGE and those of zones A and B it could be observed that the more significant protein components found in the raw product are the same in the two samples deriving from zones A and B, even though in different concentrations.

Isoelectric point

PAGE Plates LKB 3.5–9.5 were used according to the supplier's instructions.

Unfractioned LGE gave one slight band at pH 8.3, one marked band at pH 6.7–7 and several close bands between pH 6 and 4.5 having the typical aspect of isoantigens.

LGE zone A gave one marked band at pH 8.2, one marked band at pH 6.7 and some bands in acid zone with a certain prevalence of 3 particular bands at pH 5.6; 5 and 4.9.

LGE zone B showed a remarkable intensity of staining of the zone in the acid zone at pH<6 with a typical aspect of isoantigens.

Biochemical, immunochemical and radioimmunological results

Doses of 5 ml (corresponding to 1 mg of dry extract) were prepared from the solution obtained before the concentration step and were emulsified with Freund's complete adjuvant. 2 Rabbits were immunized with a dose every 15 days.

Figure 8:
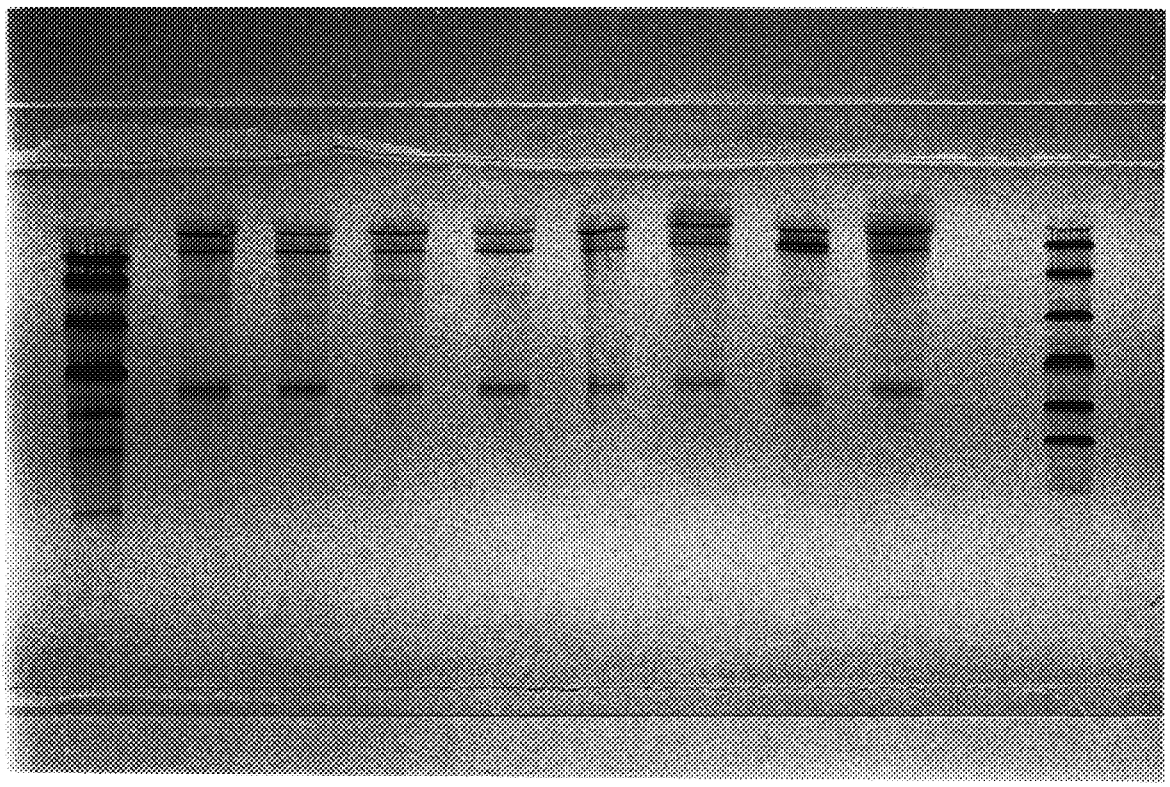
FIG. 8 is a diagram of a PAGE 4/30 test results of the Example.

Of the two original rabbits, one was lost after the first immmunization. From the second animal an aliquot of serum (called RF4) was obtained, that was then used for biochemical, immunochemical, radioimmunological and immunocytochemical studies. The RF4 antibody was tested with the Western Blot method against LGE. The antigen was submitted to PAGE SDS PAA 4/30 plates (Pharmacia) and subsequently transblotted into Nitrocellulose. This last was then incubated with RF4 serum and the reaction was revealed with antirabbit peroxydase (PIERCE). As shown FIG. 8, the antibody recognizes proteins of about 50.000 d molecular weight.

A second group of rabbits was immunized with LGE as described above (5 ml, corresponding to 5 mg of dry extract, emulsified with 2.5 ml of Freund's complete adjuvant).

These rabbits yielded fourteen antisera called anti-LGE 1, 2, 3, 4, 5, 6, 7, 8, 9, 10, 11, 12, 13, 14 which were tested in the same way as RF4.

Figure 9:
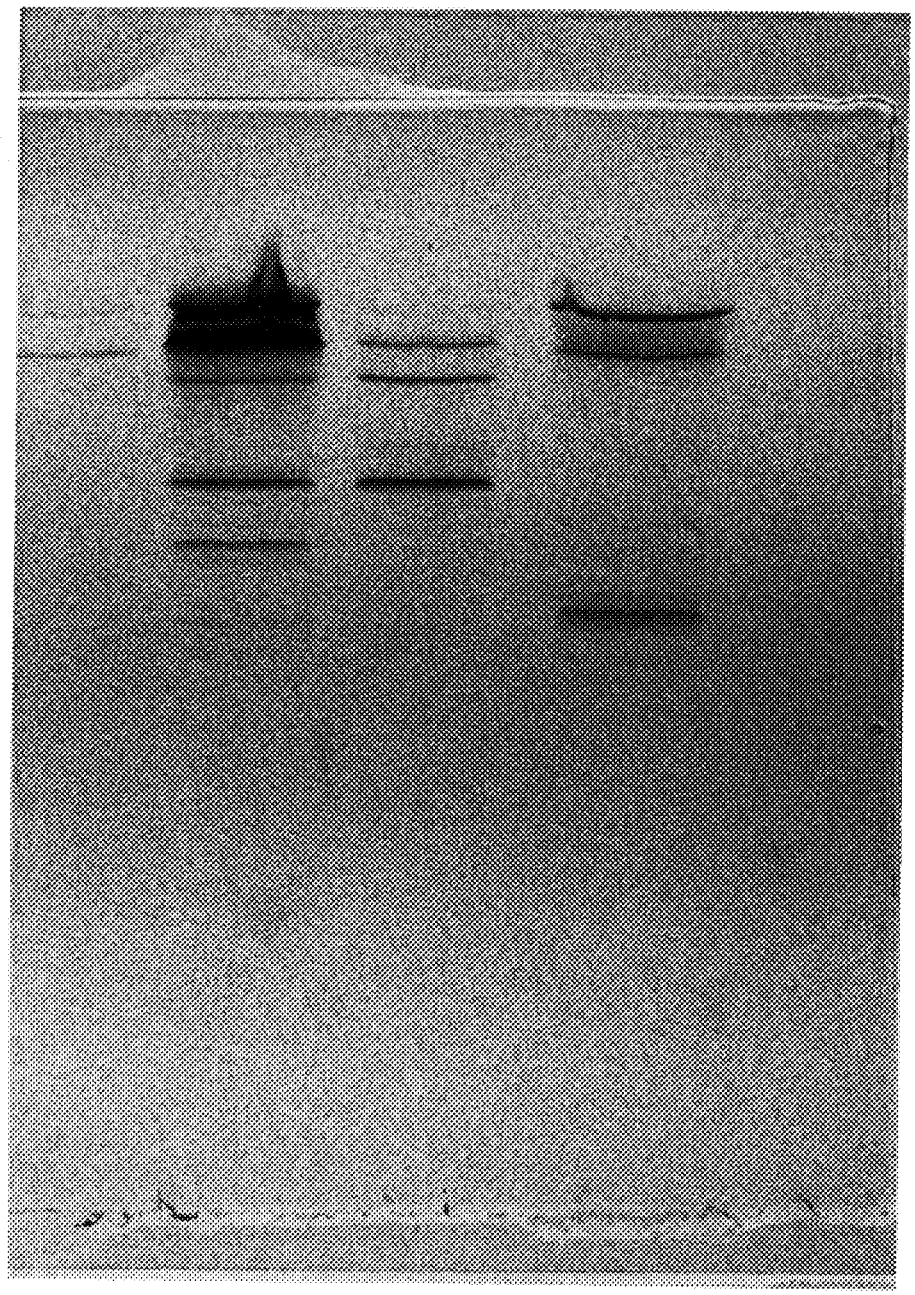
FIG. 9 is a diagram of a PAGE 4/30 test results of the Example.

The data obtained from the biochemical methods (in particular, the Western Blot one) suggest that these antisera, unlike the RF4 antiserum, recognized all the proteins components of LGE (FIG. 9).

Moreover, female BALB/c mice 10 week old were immunized for the production of monoclonal antibodies. Particularly, two mice were immunized with LGE (1 mg/ml) and two were immunized with LGE zone A from DEAE 5PW (1 mg/ml), by subcutaneous administration of 100 μl of antigen+100 μl of Freund's Adjuvant.

The immunization scheme is reported hereinbelow:

$1^{st}$ administration: 100 μl of Ag+100 μl of complete Freund's Adjuvant.

$2^{nd}$ administration: 100 μl of Ag+100 μl of complete Freund's Adjuvant. 7 days after the 1st administration $3^{rd}$ administration: like $2^{nd}$. 7 days after the $2^{nd}$ administration $4^{th}$ administration: like $3^{rd}$. 7 days after the $3^{rd}$ administration.

Figure 10:
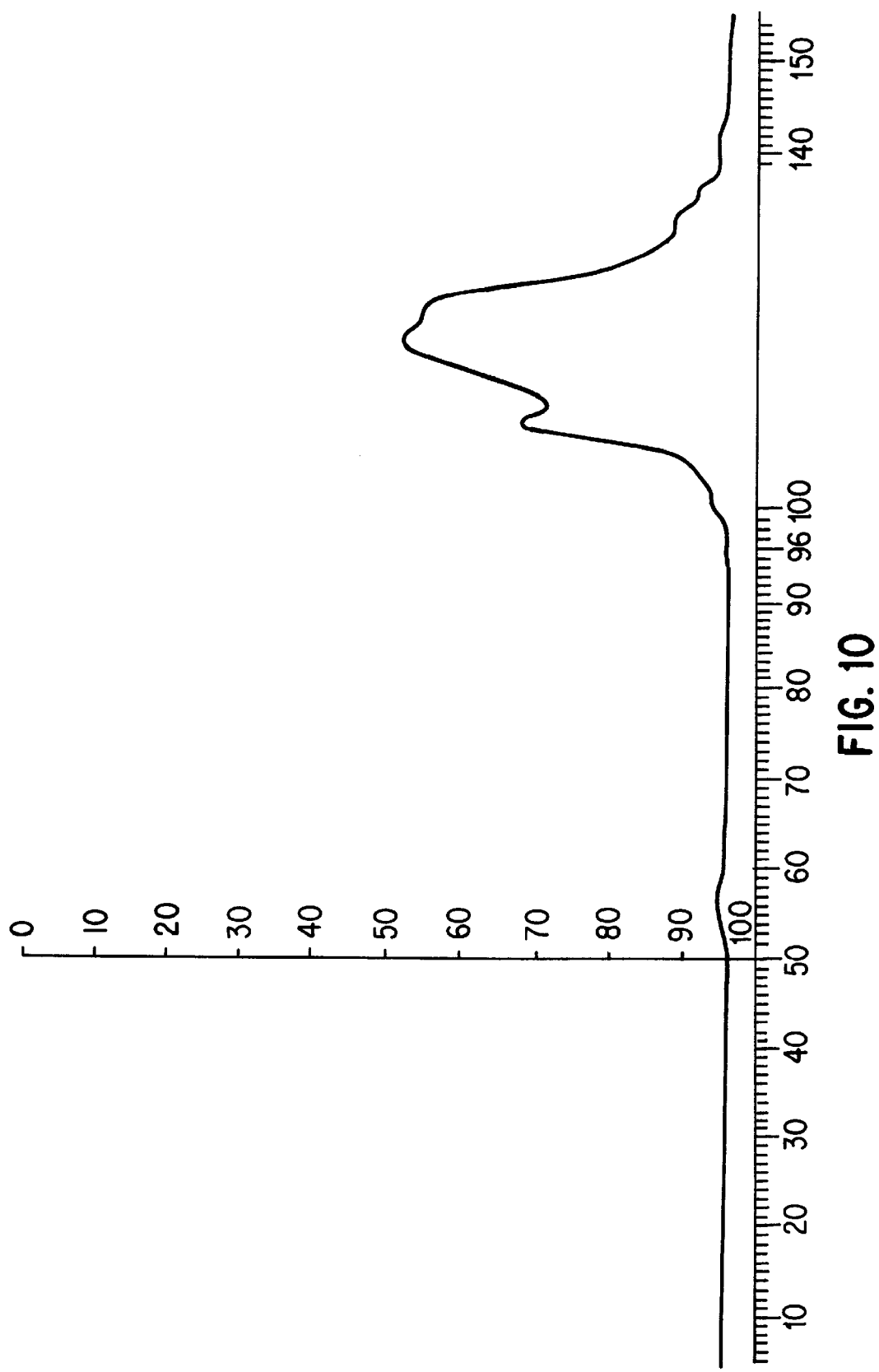
FIG. 10 is a diagram of binding test results of the Example.

At the end of immunizations an aliquot of blood was taken from each mouse and the sera obtained were subjected to the binding test against LGE (FIG. 10) and to immunocytochemical tests.

Based on the obtained results, it was decided to sacrifice mouse n. 2, immunized with LGE zone A, in order to obtain monoclonal antibodies.

Fusion performed according to Milstein gave 250 clones. A first screening showed that many clones were directed towards the determinants expressed on the LGE low molecular weight components, whereas a lower number of clones recognized the 50.000 d protein. The $2^{nd}$ screening, carried out after clone expansion, gave negative results for all the clones, therefore, it was decided to fuse the spleen from another immunized mouse. The fusion gave 400 clones (100%). In the first test, after approximately 10 days, 64 clones proved to be positive on LGE.

The supernatant of these 64 clones was subsequently tested on LGE, LGE zone A and LGE zone B. The screening showed 4 clones to exhibit a strong binding to 3 antigens, more evident on LGE zone A. These 4 clones were cloned and then retested in the same way on the three antigens. In parallel, the clones were also tested on LGE in Western Blot.

The results from these two tests led us to expand and produce the ascites of 9 clones. The obtained ascites were titrated with the binding test against LGE, LGE zone A and LGE zone B. All the ascites exhibited a good degree of binding to the three antigens, with a certain prevalence for LGE zone A.

On the contrary, the Western Blot test showed that only one monoclonal antibody was able to bind a 50.000 d band, while all the other ones recognized a band with a molecular weight slightly exceeding 50.000 d. At variance with the binding test, none of these monoclonal antibodies showed any binding to the low molecular weight components. A study with "nude" mice subjected to tumor implantation (human colon adenocarcinoma cell line named HT29) was carried out.

10.000.000 Cells in 0.5 ml of medium were inoculated into each animal. Seventeen days after inoculation the animals were treated with the RF4 antiserum previously purified by ion exchange, in order to isolate the immunoglobulin fraction, and then radiolabelled with $^{125}$I. Each animal received 10.000.000 cpm in 0.5 ml PBS+1% BSA intraperitoneally.

The animals were sacrificed after 24, 48 and 72 hours and necropsied to calculate the antibody localization index.

The capability of antigenic recognition by the sera of LGE immunized rabbits was tested on human tissues.

The antisera were tested on human tissue sections with the ABC immunoperoxydase and the immunogalactosidase procedures, and with RIA on human tissue extracts.

Sections of formalin fixed—paraffin embedded carcinomas of stomach, large intestine, breast, lung, prostate and ovary, as well as tumoral explants (obtained in nude mice) of HT29 cells (from an intestinal carcinoma), breast cancer MCF7 and GTL16 cells were employed. For control different human normal tissues were used.

From the obtained results, it could be evidenced the followings:

a) Rabbit anti-LGE sera, stained in brown, recognized superficial and cytoplasmic antigenic structures in neoplastic cells, with variable degrees of titre and specificity, in cases of gastric, large bowel and mammary carcinomas and HT29, GTL16 cells.

b) No reaction occurred between the rabbit anti-LGE sera and human normal liver cells in immunocytochemistry and with CEA in immunocytochemistry and RIA.

c) Not all tested tumors were positive.

The LGE, the $^{125}$I LGE, the rabbit anti-LGE and the rabbit $^{125}$I anti-LGE systems were tested in vivo, in nude mice and in nude mice xenografted with HT29 cells.

The results obtained were the following:

1) In both groups, $^{125}$I LGE showed in vivo a very rapid turnover; 24–48 hours after subcutaneous injection all radioactivity was localized in urinary system.

2) The LGE and the anti-LGE immunoglobulins induced no reduction of the tumor burden in nude mice, even if in same cases a marked hyperaemia of the tumor was observed.

3) $^{125}$I-labelled anti-LGE immunoglobulins showed a significant LGE localization in the neoplastic mass 3–5 days after injection in nude mice xenografted with HT29 cells. The above results reproduced in vivo the immunocytochemical data.

The extract (LGE) and the anti-LGE sera were tested in vitro on:

1) Primary cultures of human neoplastic pleural effusions.

2) Neoplastic cell lines: human (lines HMF7 and HT29) and rat (R3230Ac).

4) Basophil Degranulation Test.

The results were the following:

1) LGE and anti-LGE sera showed no direct toxic effect on neoplastic cells.

2) LGE and the anti-LGE sera showed in vitro no TNF (tumor necrosis factor) activity on target cells.

3) A cytotoxic activity, probably mediated by lymphocytes and/or macrophages, was evidenced on breast cancer cells in primary cultures of neoplastic effusion.

4) When K562 and HL60 were used as target cells, LGE acted as a strong LAX (Lymphokine-Activated Killer Cells) inducer on human lymphocytes.

This result was variable in comparison with the IL2 response. In fact lymphocytes from different donors showed different cytotoxyc effects when treated with LGE.

On the contrary, LGE and IL-2 together greatly increment this activity (+27.2%).

Experiments run with CTLL cells (I12 sensitive) exclude any type of similarity between LGE and I1-2.

No comparison could be done between LGE and any BRM (biological response modifiers), particularly those of the group 2. In fact LGE was inactive in vitro on tumor cells and in vivo on tumor cells in "nude" mice model. The in vivo response obtained with LGE on the metastatic human pleural effusion indicated that the presence of the immunity mediator cells was necessary.

On the other hand, the extraction of LGE in a high acidic medium excluded any similarity with the BRM and with interferons.

5) LGE inhibited "in vitro" the proliferation of PBL. This could be related to a direct inhibitory effect on lymphocytes or it could be mediated through the induction of different inhibitory factors. The inhibitory effects appeared to be dose and time dependent.

LGE was assayed in the basophil degranulation test. This test is used in order to recognize a specific antigen against basophils and/or attached antibodies which have acquired an immune memory. The test is considered positive for values over 30%. On blood samples of a pulmonary carcinoma patient, LGE produced in a very low concentration (1 μg–0.1 μg/ml) the significant dose dependent basophil degranulation (>80%). Tests performed on further 5 cases showed that 50% patients suffering from neoplasia were positive to this test. No degranulation occurred on controls performed with non washed (i.e. in the presence of circulating antibodies and antigens and not only with factors attached to basophils) and without calcium samples (Tab. 1). Degranulation of basophils is not present using blood of healthy donors.

TABLE 1

| L.G.E. | basophils/granulocytes % | | | % of degranulated B. |
|---|---|---|---|---|
| -whole blood | | | | |
| control | 25 | 6050 | 0.41 | |
| 100 μg/ml | 21 | 6000 | 0.35 | 15 |
| 10 μg/ml | 28 | 6900 | 0.4 | 2 |
| 1 μg/ml | 34 | 7830 | 0.43 | 0 |
| 0.1 μg/ml | 25 | 7500 | 0.34 | 15 |
| 100 μg/ml No Ca++ | 31 | 8300 | 0.37 | 7 |
| -washed blood | | | | |
| control | 46 | 8550 | 0.54 | |
| 100 μg/ml | 21 | 10000 | 0.21 | 61 |
| 10 μg/ml | 12 | 10000 | 0.12 | 78 |
| 1 μg/ml | 9 | 10000 | 0.09 | 83 |
| 0.1 μg/ml | 25 | 11000 | 0.22 | 59 |
| 100 μg/ml No Ca++ | 43 | 6300 | 0.69 | 0 |
| 10 μg/ml No Ca++ | 44 | 6500 | 0.67 | 0 |
| 1 μg/ml No Ca++ | 43 | 6300 | 0.69 | 0 |

Toxicology

Acute and chronic toxicities in animals were tested in mice and rabbits.

For acute toxicity, mice and rabbits were daily subcutaneously injected (for 10 days) with an LGE solution, equivalent to 7.1 mg/kg dose.

Chronic toxicity tests are ongoing in rabbits for six months with weekly doses of 1.2 mg/kg.

No toxic effects neither detectable alterations could be evidenced.

Preliminary studies with $^{125}$I labelled LGE demonstrated a complete clearance in 24/48 hours, through urine.

No toxic effects could be detected by injecting LGE at various concentrations to animals. A letal dose could not be determined.

Clinical tests

First Phase

29 Terminal patients were treated on a compassionate basis and with the assent of patients. All of them had previously received multiple anticancer treatments (surgery, radiotherapy, chemiotherapy) as well as after supportive treatment, such as courses of anti-inflammatory drugs (FANS and steroids) and opioids or other major analgesics.

Most patients were cachectic and ever precomatous with mean life expectance of <7 days.

Nevertheless, a positive response was observed in 70% of the patients, the most common effect being the disappearance of pain and the induction in patients of a subjective feeling of well-being; for 48% of the patients a remarkable increase of life expectancy (>2 months) was observed and no pain recurred.

The reduction of the tumoral mass was observed in 5 on 14 patients survived more than two months (Tab. 2).

TABLE 2

FIRST PHASE

| METASTASES OF and NUMBER or CASES | | RESPONSE TO L.G.E. SUBCUTANEOUS INJECTION (1,5 mg) | | |
|---|---|---|---|---|
| | | POSITIVE 30 days | POSITIVE 15 days | NEGATIVE |
| GASTROENTERIC | 8 | 3 (37,5%) | 1 (12,5%) | 3 (37,5%) |
| LUNG CANCER | 6 | 4 (66,6%) | 1 (16,6%) | 1 (16,6%) |
| BREAST CANCER | 4 | 2 (50%) | 1 (25%) | 1 (25%) |
| PANCREAS CANCER | 4 | 1 (25%) | 2 (50%) | 1 (25%) |
| GENITO-URINARY CANCER | 3 | 3 (100%) | — | — |
| SARCOMAS | 2 | — | 1 (50%) | 1 (50%) |
| VARIOUS CANCER | 2 | 1 (50%) | — | 1 (50%) |
| TOTAL | 29 | 14* (48,2%) | 6 (20,6%) | 9 (31,4%) |

*In five cases disappearance of neoplastic masses (clinico-instrumental demonstrations)

In the first group of patients, the treatment exerted highly favourable subactive effect, but no further analysis could be done because of the heterogeneicity of the pathologic, and clinical conditions, accordingly the patients were not submitted to instrumental or laboratory evaluation.

Moreover the LGE treatments ranged from the daily to the weekly administration (0.025 mg/kg). In this experience no anaphylactic reaction appeared.

From this first part of investigations, the following observations were drawn:

1) LGE showed no toxicity in man also after repeated daily administration.
2) Different batches induced the same clinical effects.
3) LGE induced an intense pain reduction with a better cenesthesis, appetite and bowel function improvement.

In the clinician opinion, it induced an unexplained "euforia" in very ill patients.

Second Phase

During this period 141 new terminal cancer patients were treated. But the attitude of the clinicians was however different basing on the assurance about the harmlessness of the LGE and the need to document the positive effects which were observed. The drug was however still administered only to terminal patients, for whom any, other treatment had failed, and on a merely compassionate basis.

Almost all patients received a single subcutaneous injection of 1.5 mg LGE (about 0.025 mg/kg). In some cases (in the last three months) a second dose was administered one month later.

In the following figures, patients were divided in 2 groups defined as "N" and "U".

The "N" patient collection represented 108 cases.

The "U" experimentation was performed on 33 patients. The definition of responders was based only on subjective and objective general condition i.e. performance status, as the patients were all with a very low life expectance.

"U" group (Tab. 3)

After 4 months, 33 terminal ca patients treated with LGE were all alive, among them 11 were considered not yet evaluable and of the remaining 22 patients, 13 were responders (3 for a period lower than one month).

Among the remaining 10 responders (>30 days), 5 were still alive with a life expectance of 6 months.

The reduction (>25%) and/or disappearance of tumor mass was shown in this group in 2 patients on 5. The 9 non-responders were all dead.

In the patients of the group "U" controls were performed on 21 patients in different times from LGE administration.

In 13 patients the granulocyte increase was statistically significant without any other lymphocytic population increase.

TABLE 3

Second phase - "U" Group

| Clinical situation | n° cases | Alive | Dead | regression or disappearance of masses (>25%) |
|---|---|---|---|---|
| NON RESPONDERS | 9 | — | 9 | — |
| RESPONDERS 30 DAYS | 10 | 5 | 5 | 2 |
| RESPONDERS 30 DAYS | 3 | — | 3 | — |
| UNDER EVALUATION | 11 | 11 | — | — |
| TOTAL | 33 | 16 | 17 | 2 |

It is necessary to remind in the evaluation of these data that these were terminal ca patients, highly immunosuppressed, and therefore the blood chemistry modification induced by LGE could be hidden or altered by previously performed immunosuppressive therapies (chemio, radiotherapy, ecc.).

"N" group (Tab. 4-5-6)

108 Terminal ca patients were treated. Every anti-tumoral specific therapy (chemio, radio, hormonotherapy) was suspended for everyone of these patients as it proved to be ineffective. Patients received only pain therapy, often opioids and FANS, which were interrupted at the beginning of this trial.

All patients received one subcutaneous single dose of LGE (1.5 mg). In some case the dose was repeated 30 days after the first administration.

Only 82 patients out of 108 treated were evaluated (Tab. 4) and among them, after 5 days of LGE treatment, 27 (32.9%) were non-responders and 52 (63.4%) were responders.

11 non-responder (13.4%) and 37 (45.1%) responder patients survived within the first 30 days from a single LGE injection (Tab. 4).

TABLE 4

Second phase - "N" Group

| METASTASIS OF | n° CASES | n° EVALUABLE CASES | 5 DAYS | 30 DAYS | 30 DAYS | - MASSES |
|---|---|---|---|---|---|---|
| GASTROENTERIC CANCER | 27 | 17 | 7–<br>9+ | 1–<br>5+ | 1–<br>5+ | 4 |
| LUNG CANCER | 22 | 17 | 5–<br>10+ | 2–<br>7+ | 0<br>5+ | 4 |
| BREAST CANCER | 20 | 16 | 4–<br>12+ | 2–<br>8+ | 1–<br>8+ | 4 |
| GENITO-URINARY CANCER | 12 | 10 | 3–<br>7+ | 2–<br>5+ | 1–<br>4+ | 4 |
| LARYNX CANCER | 3 | 2 | 2–<br>0 | 1–<br>0 | 0<br>0 | 0 |
| THYROID CANCER | 6 | 4 | 2–<br>2+ | 1–<br>1+ | 0<br>0 | 1 |
| SOFT TISSUE SARCOMAS | 4 | 3 | 2–<br>1+ | 1–<br>1+ | 0<br>1+ | 1 |
| BONE SARCOMAS | 14 | 13 | 2–<br>11+ | 1–<br>9+ | 1–<br>7+ | 6 |
| TOTAL | 108 | 82 | 27–<br>52+ | 11–<br>37+ | 4–<br>30+ | 24 |

Figure 11:
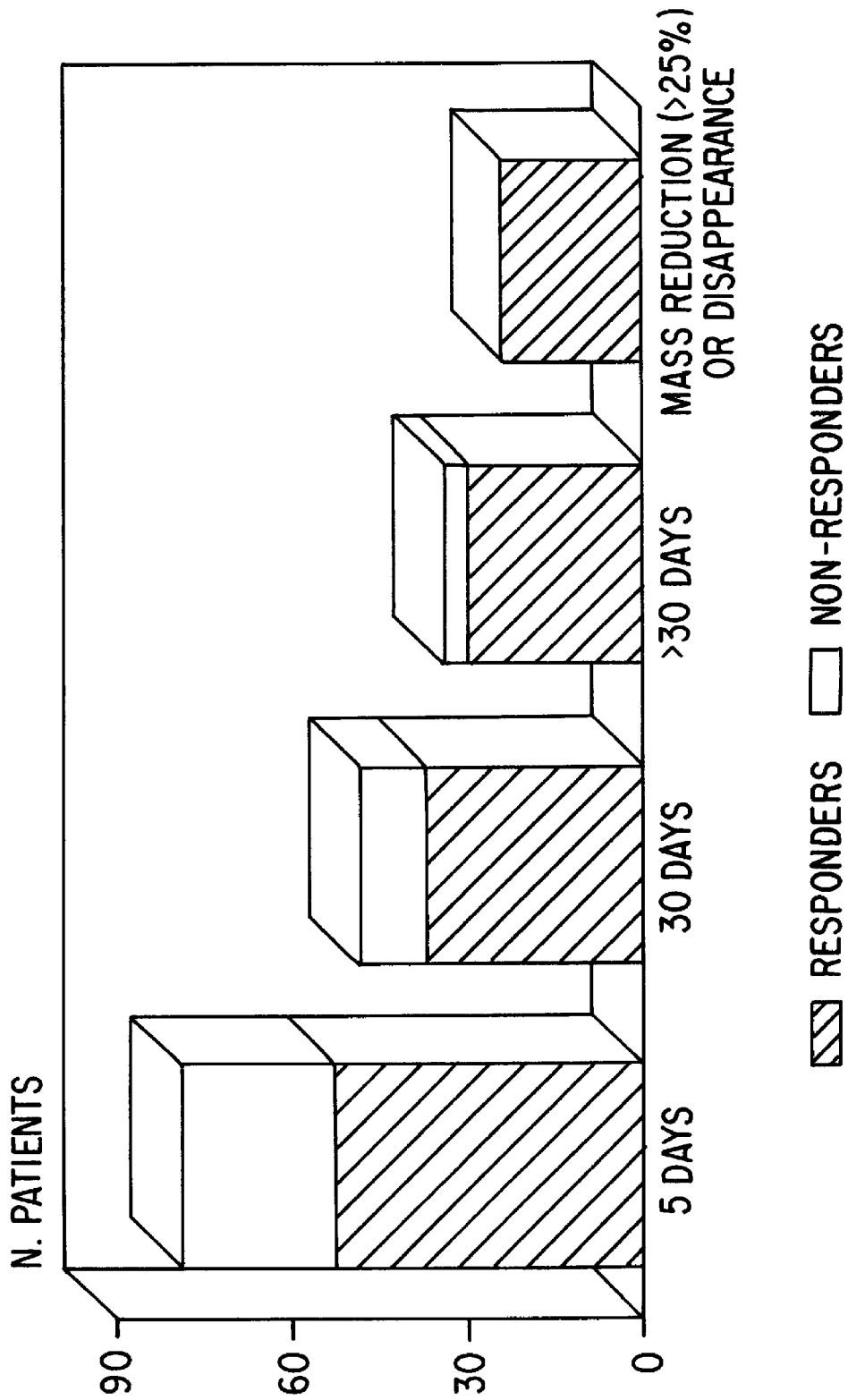
FIG. 11 is a graphical presentation of clinical test results reported in the Example.

– NON RESPONDERS PATIENTS
+ RESPONDERS PATIENTS
- MASSES: reduction (>25%) or disappearance After the first month and in the following 4 months, 4 (4.8%) non-responders and 30 responders (36.5%) survived. In 24 (80%) of the 30 responder patients with a survival more than one month also the reduction (>25%) or the disappearance of the neoplastic mass was shown (FIG. 11 and Tab. 5).

TABLE 5

Second phase - "N" Group
L.G.E. THERAPY - Relationship between Responders and neoplastic masses

| METASTASES OF | n° CASES | NON RESPONDERS | RESPONDERS (>1 month) | - MASSES* |
|---|---|---|---|---|
| GASTROENTERIC CANCER | 17 | 1 | 5 | 4 |
| LUNG CANCER | 17 | 0 | 5 | 4 |
| BREAST CANCER | 16 | 1 | 8 | 4 |
| GENITO-URINARY CANCER | 10 | 1 | 4 | 4 |
| LARYNX CANCER | 2 | 0 | 0 | 0 |
| THYROID CANCER | 4 | 0 | 1 | 1 |
| SOFT TISSUE SARCOMAS | 3 | 0 | 1 | 1 |
| BONE SARCOMAS | 13 | 1 | 7 | 6 |
| TOTAL | 82 | 4 | 30 | 24 |

* - MASSES: reduction (>25%) or disappearance

In these patients, the symptom "neoplastic pain" was studied independently of all other symptoms scored in order to define the patient as responders.

Tab. 6 shows the results of this study on 82 patients which confirms the previous observation: in the remarkable percentage of cases, 37/82 (45.1%), the pain often resistant to the most important opioid and to the recent pain therapies, disappeared within 12/24 hours and in any case always within the first days.

In an other smaller patient group (24/82), the neoplastic pain disappearance was always complete but it disappeared later (within 30 days).

TABLE 6

Second phase - "N" Group
L.G.E. THERAPY - Disappearance of neoplastic pain

| METASTASES OF | n° EVALUABLE CASES | UP TO 5 DAYS | UP TO 30 DAYS |
|---|---|---|---|
| GASTROENTERIC CANCER | 17 | 9 | 6 |
| LUNG CANCER | 17 | 9 | 5 |
| BREAST CANCER | 16 | 9 | 2 |
| GENITO-URINARY CANCER | 10 | 5 | 3 |
| LARYNX CANCER | 2 | 0 | 0 |
| THYROID CANCER | 4 | 2 | 1 |
| SOFT TISSUE SARCOMAS | 3 | 1 | 1 |
| BONE SARCOMAS | 13 | 2 | 6 |
| TOTAL | 82 | 37 | 24 |

Third Phase

Although the patients were controlled following the same criteria listed above, the anatomo-phathologic evaluation of the treatment was introduced. Six patients suffering with different cancers who received a single injection of LGE were submitted to surgery for the exeresis of the tumoral mass after an interval ranging from 4 to 51 days.

A total of 8 specimens was examined, from 6 patients.

2 Specimen tissues (both from patients affected by carcinoma of the large intestine) were obtained before treatment.

From the same patients, as well as from other 4 patients affected by gastric carcinoma (2 cases), carcinoma of anal tract and of carcinoma of the pancreas, tissues were examined after LGE treatment (injection made from 4 to 51 days before).

Tissues were embedded in paraffin and histologically examined. In addition, immunostaining with monoclonal antibodies against lymphocytes (common leucocyte antigen CLA), PAN P marker (L26 monoclonal), PAN T marker (VCHL1 monoclonal) were performed.

The results indicate that:

neoplastic tissues obtained before LGE treatment, showed only a modest inflammatory infiltrate.

The same patients were treated with LGE.

The tissues examined 15 days after LGE treatment showed extensive areas of necrosis and prominent infiltrate of granulocytes.

The same results were obtained in tissues from different patients 51 days after LGE treatment.

In all cases, independently by the time of examination after LGE treatment, granulocyte infiltration by eosinophilic granulocytes was quite obvious. Staining of different types of lymphocytes showed presence of CLA positive cells, mainly of B type lymphocytes, while UCHL1 cells (T lymphocytes) were rare.

This low number of T lymphocytes combined with the presence of granulocytes and eosinophiles seems to be extremely interesting when compared with haematochemical values of patients in therapy (granulocytes increase during first days after LGE administration) and with the results from PBL cultures in presence of LGE where an inhibition of PBL proliferation has been observed and results of basophil degranulation test.

Clinical Conclusion

The results obtained in 3 multicentric trials were quite homogeneous.

The amount of responders after one month of observation was, respectively, of 48.2%, 45.4% and 45.1% although there was the difference in time, procedure and doctor culture.

The overall response after every observation period, including the <7 days group, was respectively 68.9%, 59% and 63.4%.

Figure 12:
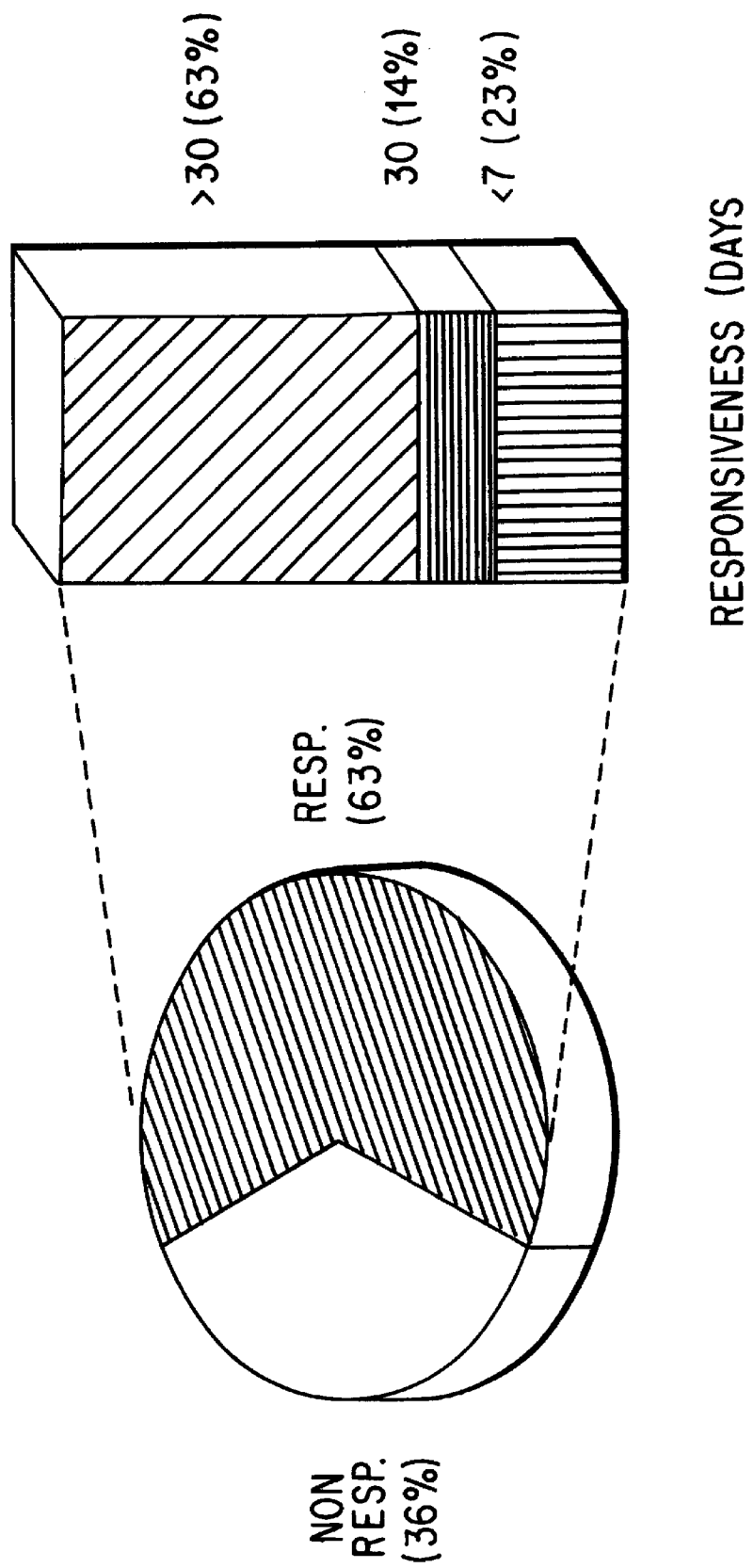
FIG. 12 is a graphical presentation of clinical test results reported in the Example.

An overall response rate (FIG. 12) of 46% (observation period 1 month) and 63.4% of total responders was obtained.

It is interesting to remember that in the "N" group (Tab. 4 and 5) 80% of the responders with more than one moth of survival showed a reduction (>25%) or disappearance of tumor mass.

In the same observation period only 4.8% of the non-responders survived.

A very unusual and astonishing observation is the dramatic (Tab. 7) disappearance of neoplastic pain also in subjects without response to opioid.

This effect begins before the reduction of tumor mass and it is present also in those patients in which no objective effect was seen.

TABLE 7

LGE THERAPY: single subcutaneous injection (1,5 mg)
CLINICAL RESULTS ON 134 PATIENTS

|  |  |  | reduction or disappearance of masses |
|---|---|---|---|
| RESPONDERS | 85 | <7 DAYS: 19 | — |
|  |  | 30 DAYS: 12 | — |
|  |  | >30 DAYS: 54 | 31 |
| NON RESPONDERS | 49 |  |  |

It is worthwhile to study deeper this clinical observation.

The results of third trial show an intensive granulocytosis and perivascular necrosis in the neoplastic tissue after administration of single dose of LGE and confirm, from an histopathological point of view, the substance activity in inducing the lysis of neoplastic cells in man with a tumor specific mechanism and inducing immunogenic pattern in the host.

We claim:

1. A preparation containing extracts of polypeptide nature obtainable by extraction with $HClO_4$ and 3M KCl from goat liver homogenates, which extracts have the following characteristics:

molecular weight ranging from 10,000 to 50,000 daltons (by polyacrylamide gel electrophoresis) and electrophoretic bands on polyacrylamide gel of about 50,000, 20,000, 14,800 and 12,000 daltons;

capable of inducing the formation of antibodies which specifically bind in vivo or in vitro antigens which are present in human tumoral cells, when administered to different animal species;

capable of affecting pain, induce an effect of cell lysis, and inhibit or slow tumor growth, when administered to humans affected by malignant tumors of different kinds.

2. Pharmaceutical compositions comprising a pharmaceutically acceptable carrier and, as the active ingredient, the extracts of polypeptide nature as claimed in claim 1.

3. A method for treatment of an animal having a tumor and for control of tumor related pain, comprising administering to the animal a tumor treatment or pain-reducing effective amount of the extracts of claim 1.

* * * * *